United States Patent [19]

Pannu

[11] E Patent Number: Re. 32,525

[45] Reissued Date of Patent: Oct. 20, 1987

[54] UNIVERSAL INTRAOCULAR LENS AND A METHOD OF MEASURING AN EYE CHAMBER SIZE

[76] Inventor: Jaswant S. Pannu, 6120 Almond Ter., Plantation, Fla. 33317

[21] Appl. No.: 797,656

[22] Filed: Nov. 13, 1985

Related U.S. Patent Documents

Reissue of:

[64] Patent No.: 4,435,855
Issued: Mar. 13, 1984
Appl. No.: 261,953
Filed: May 8, 1981

U.S. Applications:

[63] Continuation-in-part of Ser. No. 136,243, Apr. 1, 1980, abandoned.

[51] Int. Cl.[4] ..... A61F 2/16; A61B 5/10

[52] U.S. Cl. ..... 623/6; 33/512; 128/774

[58] Field of Search ..... 623/6; 128/774; 33/511, 33/512

[56] References Cited

U.S. PATENT DOCUMENTS

| | | | |
|---|---|---|---|
| 3,971,073 | 7/1976 | Richards et al. | 3/13 |
| 4,073,014 | 2/1978 | Poler | 3/13 |
| 4,092,743 | 6/1978 | Kelman | 623/6 |
| 4,110,848 | 9/1978 | Jensen | 3/13 |
| 4,159,546 | 7/1979 | Shearing | 623/6 |
| 4,174,543 | 11/1979 | Kelman | 623/6 |
| 4,249,271 | 2/1981 | Poler | 623/6 |
| 4,253,200 | 3/1981 | Kelman | 623/6 |
| 4,254,510 | 3/1981 | Tennant | 623/6 |
| 4,304,012 | 12/1981 | Richard | 623/6 |
| 4,319,564 | 3/1982 | Karickhoff | 128/774 |
| 4,363,143 | 12/1982 | Callahan | 623/6 |

FOREIGN PATENT DOCUMENTS 2717706 10/1978 Fed. Rep. of Germany ..... 3/13

OTHER PUBLICATIONS

The Intraocular Implant Lens Development and Results with Special Reference to the Binkhorst Lens, by Marcel E. Nordlohne, The Williams & Wilkins Co., 1975 (Book) pp. 14–20.

The Rayner Choyce Mark VIII Anterior Chamber Implant Catalogue No. 469, Rayner & Keeler Limited (3 pages).

The Linstrom Centrex Style 20 Posterior Chamber Lens, Surgidev Corp., Santa Barbara, Calif.

"Nuevos Modelos de Lentes Plasticas de Camara Anterior" by Joaquin Barraquer et al, Anales del Instituto Barraquer, Sep. 1961, pp. 345–351, (FIG. 9 on p. 348).

*Primary Examiner*—Ronald L. Frinks
*Attorney, Agent, or Firm*—Banner, Birch, McKie & Beckett

[57] ABSTRACT

A universal intraocular lens that may be implanted in an eye, in an anterior chamber, in a posterior chamber and in any size eye chamber wherein a tangential flexible strand is attached to a lens at one end and the other free end is formed into a snag resistant ring, or disc which is approximately circular to avoid injury to delicate eye tissue during implantation, centration or removal of said lens.

11 Claims, 9 Drawing Figures

UNIVERSAL INTRAOCULAR LENS AND A METHOD OF MEASURING AN EYE CHAMBER SIZE

Matter enclosed in heavy brackets [ ] appears in the original patent but forms no part of this reissue specification; matter printed in italics indicates the additions made by reissue.

BACKGROUND OF THE INVENTION

This application is a continuation-in-part of application Ser. No. 136,243 which was filed on Apr. 1, 1980 and now abandoned by applicant. The content of said application is incorporated in this application.

An intraocular lens is normally implanted in the anterior or posterior chamber of an eye following extraction of a cataractous lens. Since replaceable lenses are different for use in a posterior chamber than use in an anterior chamber, two different lenses must be kept in stock. In addition, the eye chamber could vary in size, again requiring additional varied sizes in stock.

The most widely used Shearing type lenses are utilized only for posterior chamber implantation. It is a plastic lens having two opposed flexible strands, one a superior loop and the other an inferior loop, wherein the free ends are arched and end in a point. This makes it extremely difficult for a surgeon to master the implantation of the superior loop during realignment or removal of the lens without injuring the delicate tissue of an eye.

One of the main objects of this invention is to avoid this snagging point of the loop by replacing it with a snag resistant disc, ring or closed circular loop.

Another object is to provide such a snag resistant strand so that both right and left handed surgeons may be able to use the same lens, thus eliminating the need for a specially designed lens for a left handed surgeon.

Another object is to provide a universal lens that can be used in an anterior or posterior chamber of an eye and can be equally used in a small, medium or large eye chamber size, thus avoiding the stocking of a large number of different types and sizes by hospitals and surgeons.

Another object is to provide just one type of universal lens for all eye transplants so that all surgeons will become familiar with it and greater safety can be provided for the patients.

Another object is to so tangentially shape the flexible strand as to cause the lens to self-center when implanted.

A further object is to use the distance between the ring edge and the lens edge to determine the size of an eye chamber.

Details of this invention will become more readily apparent from the following description when taken in conjunction with the accompanying drawings:

IN THE DRAWINGS

Figure 1:
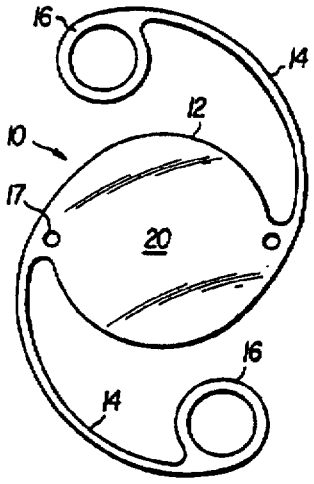
FIG. 1 is an illustration of the intraocular lens of this invention in a front elevational view.
Figure 2:
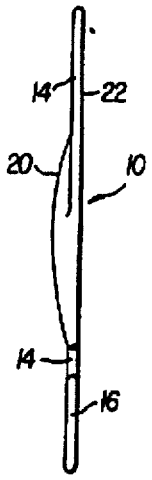
FIG. 2 is a side elevational view of the lens of FIG. 1.

In FIG. 1, there is shown intraocular lens 10 of this invention, having a lens body 12 measuring 6 mm in diameter and centration openings 17 that measure 0.25 mm in diameter which may be used for alignment of the lens during implantation of the lens. The lens is formed of clinical quality of polymethymethacrylate and has an overall length of 13.5 mm inclusive of the flexible strands 14 which are tangentially curved towards the lens circumference to the left on the superior strand while the inferior strand is tangentially curved to the right. This enables a surgeon to implant the lens with minimal force and permits the lens to be self-centering. The snag resistant looped disc 16 and strand 14 are integrally molded to the body of the lens. The thickness of the strand is 0.25 mm and the lens thickness is 0.85 mm as shown in FIG. 2.

Figure 3:
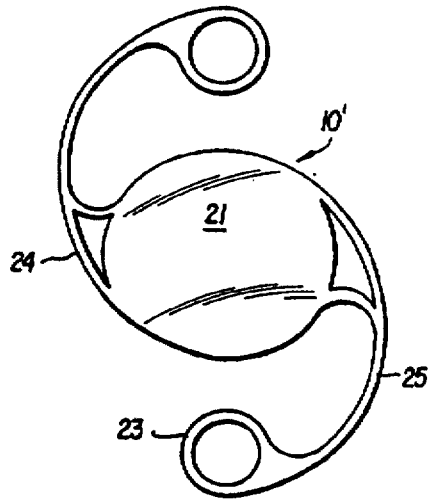
FIG. 3 is another form of the lens in a front elevational view.
Figure 4:
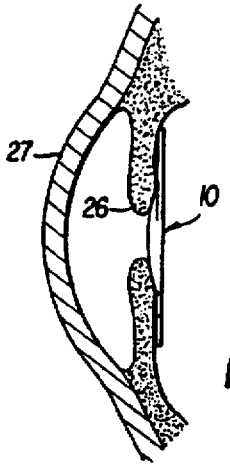
FIG. 4 is a cross-sectional schematic view of a human eye with the lens of this invention implanted in the posterior chamber.

In FIG. 3, there is shown another form of the intraocular lens 10' of this invention. The body 21 of the lens and the resilient strands 25 supporting the snag resistant rings 23 are integrally molded to the lens body, however to provide a sturdier base 24, the shape is molded into a triangular design which supports the flexible strand and said strand is shaped to be tangential to the lens circumference. In use, this lens is an actual commercial model and upon implantation, it automatically becomes self centered. It is essential that this ring be at least three times greater than the width of the flexible strand and at least one-fifth as great as the width of the lens to result in smoothly guiding the snag resistant ring across the iris or other eye tissue when implanting the lens in either an anterior or posterior chamber which is small, medium or large. When this lens is implanted into a posterior chamber as shown in FIG. 4, the snag resistant free end rings will snugly fit into the pocket found near the stationary zone of the iris 26. The lens when so implanted is self-centering and the rings lie in a plane sufficiently close to the plane of the lens so that the rings and the lens can snugly fit into the eye chamber without causing any spring back or buldging forward which would injure delicate eye tissue.

Although centration holes are normally provided on such lenses, the lens of this invention can dispense with such holes because with the ring structure and the tangentially shaped resilient strands, the [right] *ring* is self centerable.

Figure 5:
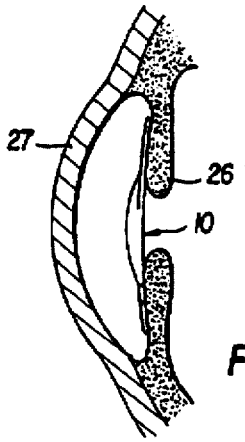
FIG. 5 is a similar cross-sectional schematic view of a human eye with the same lens implanted in an anterior chamber.
Figure 6A:
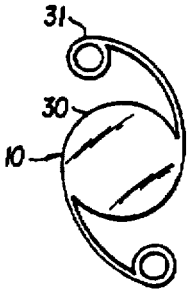
FIG. 6A to D is a schematic cross-sectional view to illustrate how the eye chamber is measured for size.
Figure 6B:
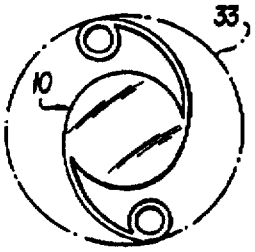
Figure 6C:
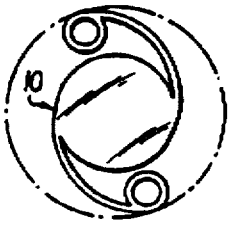
Figure 6D:
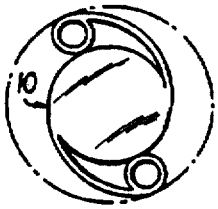

In FIG. 5, there is shown the implantation of this novel lens into an anterior chamber of an eye. The snag resistant free end of the tangential strand fits snugly in the corners between the mobile zone of the iris 26 and the cornea 27. In this instance, the lens is again self centering because of the same factors present in the posterior implantation.

Because of the ring shaped free end it is possible to use this lens for the first time to measure the size of the eye chamber.

In FIG. 6, there is shown a schematic illustration of how to measure the size of an eye chamber. In (a) there is shown the lens of this invention having a lens body whose diameter is 6 mm and whose ring diameter is 2.5 mm. In (b) such a lens is implanted in an eye chamber 33. The distance between the loop and the lens edge is measured to be 1 mm. When added together, it measures a 13 mm eye chamber size which is a large chamber size. In (c), wherein the ring to lens distance is less, a 12 mm eye chamber is measured which is a medium chamber size. In (d), wherein the ring and lens edges meet, the eye chamber measures 11 mm which is a small chamber size. To aid in sighting for measuring, it is helpful to slightly tint the snag resistant rings, however they could also be clear.

To sum up, there are many advantages in using the lens of this invention over any of the prior art lenses.

The most important advantage is the provision of a snag resistant loop which prevents injury to delicate eye tissue during implantation, centration, or removal of the lens.

The lens of the Shearing type requires more maneuvers, skill and a longer learning process for surgeons to master when inserting the superior loop of the lens, thus resulting in increasing the chance for injuring delicate eye tissue. These objections are eliminated when the snag resistant lens of this invention is used. It would be relatively easy for a surgeon to master the implantation, centration or removal of this lens without injury to delicate eye tissue.

Another advantage is that only a small force is needed by the surgeon to position the superior snag resistant ring during implantation. The tangentially curved resilient strands and the snag free loose end of the strand transfers this force into a circular movement of the lens body resulting in self centering of the lens with avoidance of undue pressure on the zonules below.

Since the lens of the invention is one that is a universal lens, a surgeon who is a novitiate will find this lens especially helpful because this lens is not only self-centering but also needs only minimal manipulation during implantation in an eye chamber.

Implantation of this new lens avoids the spring back which is present in the Shearing type lens which results in decentration. This lens, because of its tangentially formed strands, changes the downward force into a circular motion, thus avoiding any spring back landing to cause decentration.

All conventional posterior lenses are more easily implanted through a dilated pupil. The new snag free lens can be implanted through a dilated or a miotic pupil with equal ease.

If during a cataract operation, the delicate tissue of an eye is ruptured, use of the Shearing type lens with its free pointed end presents added danger of extending the tear because the free pointed end can slide further into the vitreous cavity. The snag resistant ring of this new lens avoids this difficulty.

In addition, while operating to be safe, the surgeon may decide to use this lens in the anterior chamber to avoid aborting the implantation procedure. This cannot be done with any of the prior art lenses. However, it can be done if the surgeon is using the lens of this invention.

The lens of this invention is the first universal lens implant since it can be implanted in any size of eye chamber, in a posterior chamber or in an anterior chamber. A tremendous saving in the stocking of an unduly large supply of lenses for surgeons and hospitals. Only the snag resistant lens of this invention need be stocked. No necessity now to stock many different sizes, a posterior lens and an anterior lens. All the different lenses have now been replaced with only one lens, a universally useful lens.

Finally, this novel lens can be used to determine the size of an eye chamber. This has never been possible before this lens. By merely measuring the distance between the edge of the loop and the edge of the lens with a microscopic chronometer and adding thereto the diameter of the ring and lens, the size of an eye chamber can be determined. No lens in the prior art is capable of effecting this result.

Those skilled in the art will also readily appreciate that there are various other modifications and adaptations of the precise form of the lens herein shown. For example, the ring which is approximately circular, could also be elliptical and would thus be equally useful with all the accompanying advantages so long as it is snag resistant.

What is claimed is:

1. An intraocular lens comprising:

a lens body;

at least two spaced flexible positioning and supporting elements integrally formed with said lens body as a one-piece construction and extending radially, outwardly from the periphery of said lens body;

said elements [defining a continuous, substantially circular arc having a diameter greater than the diameter of said lens body, said arc curved toward said lens circumference and] terminating in a free end spaced from said periphery; and snag-resistant means integrally formed on the free end of *each of* said elements for smoothly guiding and positioning the lens across contacted eye tissue when implanting the lens, said snag resistant means having an uninterrupted, continuously, smoothly curved outer periphery which merges with said free end and is [substantially] *at least three times* greater in [size] *width* than the width of said flexible elements, *said snag resistant elements and said positioning and supporting elements being substantially coplanar.*

2. An intraocular lens as recited in claim 1 wherein there are two of said flexible positioning and supporting elements and said elements are positioned opposite one another.

3. An intraocular lens as recited in claim 1 wherein said snag-resistant means comprise a circular disc.

4. An intraocular lens as recited in claim 3 wherein said disc has an opening therethrough.

5. An intraocular lens as recited in claim 3 wherein said disc has a diameter which is at least three times greater than the width of said flexible elements and at least one-fifth as great as the width of said lens body.

6. An intraocular lens as recited in claim 1 wherein said flexible elements contain a support member integrally formed with said flexible elements and the periphery of said lens body, said support member joined to said flexible element at a position remote from the point where said flexible element contacts the periphery of said lens body, thus defining a substantially triangular support base for said flexible element.

7. An intraocular lens as recited in claim 3 wherein said circular disc and said lens body lie in substantially the same vertical plane.

8. An intraocular lens as set forth in claim 1 wherein said flexible elements and said snag-resistant means are made from a clear material.

9. An intraocular lens as set forth in claim 1 wherein said flexible elements and said snag-resistant means are made from a colored material.

10. A method of measuring the size of an eye chamber by implanting a lens having tangentially resilient strands on opposed sides of an intraocular lens attached to the body of said lens; wherein the free end is connected to a snag resistant ring, adding the diameter sizes of said ring and said lens to the distance between the edge of said ring and the edge of said lens in mm. to determine the size of said eye chamber in mm.

*11. An intraocular lens as recited in claim 1 wherein said elements define a continuously curved arc, said arc curved toward said lens circumference.*

* * * * *